US009642825B2

(12) United States Patent
Owoc

(10) Patent No.: US 9,642,825 B2
(45) Date of Patent: May 9, 2017

(54) BIO-AVAILABLE N-ACETYL CREATINE SPECIES AND COMPOSITIONS THEREOF

(71) Applicant: 4141 HOLDINGS, LLC, Weston, FL (US)

(72) Inventor: John H Owoc, Weston, FL (US)

( * ) Notice: Subject to any disclaimer, the term of this patent is extended or adjusted under 35 U.S.C. 154(b) by 74 days.

(21) Appl. No.: 14/192,734

(22) Filed: Feb. 27, 2014

(65) Prior Publication Data

US 2015/0238453 A1     Aug. 27, 2015

(51) Int. Cl.

| | | |
|---|---|---|
| A61K 31/195 | (2006.01) | |
| A61K 31/198 | (2006.01) | |
| A61K 9/70 | (2006.01) | |
| A61K 9/00 | (2006.01) | |
| A61K 9/06 | (2006.01) | |
| A61K 9/14 | (2006.01) | |
| A61K 9/19 | (2006.01) | |
| A61K 9/48 | (2006.01) | |
| A23K 20/142 | (2016.01) | |
| A61K 31/00 | (2006.01) | |
| A23L 33/175 | (2016.01) | |

(52) U.S. Cl.
CPC .......... *A61K 31/198* (2013.01); *A23K 20/142* (2016.05); *A23L 33/175* (2016.08); *A61K 9/0095* (2013.01); *A61K 9/06* (2013.01); *A61K 9/148* (2013.01); *A61K 9/19* (2013.01); *A61K 9/4858* (2013.01); *A61K 9/7084* (2013.01); *A61K 31/00* (2013.01)

(58) Field of Classification Search
USPC ........................................................ 514/563
See application file for complete search history.

(56) References Cited

U.S. PATENT DOCUMENTS

| | | | | |
|---|---|---|---|---|
| 6,475,514 | B1 * | 11/2002 | Blitzer | A23L 1/30 424/449 |
| 7,956,031 | B2 * | 6/2011 | Naidu | A23L 1/034 424/94.1 |
| 8,372,821 | B2 | 2/2013 | Owoc | |
| 8,435,963 | B2 | 5/2013 | Owoc | |
| 8,445,466 | B2 | 5/2013 | Owoc | |
| 2007/0253941 | A1 * | 11/2007 | Naidu | A61K 31/12 424/94.1 |
| 2011/0251280 | A1 * | 10/2011 | Owoc | A61K 9/0014 514/563 |

* cited by examiner

*Primary Examiner* — San-Ming Hui
(74) *Attorney, Agent, or Firm* — Allen F. Bennett; Bennett Intellctual Property

(57) ABSTRACT

Creatine derivatives and compositions containing a bioactive form of creatine. The new chemical entity comprises an acetyl creatine, N-acyl creatines, N,N-diacyl creatines or any N-acetyl creatine species with enhanced solubility and bioavailability. Also provided by this invention are various methods for providing several beneficial effects that comprise administering compositions comprising N-acetyl creatine, N-acyl creatines, N,N-diacyl creatines or any N-acetyl creatine species to a mammalian subject, either chronically or acutely.

12 Claims, 1 Drawing Sheet

BIO-AVAILABLE N-ACETYL CREATINE SPECIES AND COMPOSITIONS THEREOF

BACKGROUND OF THE INVENTION

Field of Endeavor

The present invention relates to creatine derivatives and methods for uses thereof. More particularly, the invention relates to creatine derivatives soluble in aqueous solutions such as acetylated creatine species in the form of acetyl creatine, N-acyl creatines, N,N-diacyl creatines, acetyl creatyl peptides and their aliphatic esters with enhanced solubility that are more bioavailable than any other existing creatine derivative.

Background Information

Many nutritional supplements are available at various retail outlets, in many different delivery and dosage forms, including, but not entirely limited to tablets, capsules, powders, packets, and various other liquids formats including beverages emulsions, concentrates, and shots intended for human consumption.

One nutritional supplement is creatine, whose International Union of Pure and Applied Chemistry (IUPAC) name is 2-(carbamimidoyl-methyl-amino) acetic acid, (Chemical Abstract Services (CAS) No. 57-00-1). Creatine occurs naturally in muscle and brain, and is believed to be an essential component in energy-producing metabolism and normal muscle function and growth, and plays a pivotal role in the storage of phosphate-bound energy in the brain. It is also believed by many to be useful to bodybuilders and other athletes desiring to increase strength, increase muscle mass and/or improve performance.

In a thorough scientific review published in the Journal of Strength and Conditioning, scientists looked at 22 published studies. The average increase in muscle strength following creatine supplementation plus resistance training was 8% greater than the average increase in muscle strength following placebo ingestion during resistance training (20% vs. 12%). Also, the average increase in weightlifting performance (maximal repetitions at a given percent of maximal strength) following creatine supplementation plus resistance training was 14% greater than the average increase in weightlifting performance following placebo ingestion during resistance training (26% vs. 12%). The increase in bench press 1 RM (one rep maximum lift) ranged from 3% to 45%, and the improvement in weightlifting performance in the bench press ranged from 16% to 43%.

In another study, scientists tested the hypothesis to evaluate if five grams of oral creatine supplementation taken daily for six weeks would enhance intelligence test scores and working memory performance in 45 young adult, vegetarian subjects in a double-blind, placebo-controlled, cross-over design. Creatine supplementation had a significant positive effect on both working memory (backward digit span) and intelligence (Raven's Advanced Progressive Matrices), both tasks that require speed of processing.

Creatine supplementation has be shown to have neuroprotective effects in neurological diseases such as Huntington's disease, Parkinson's disease, and amyotrophic lateral sclerosis. Another investigation found that five grams of creatine supplementation daily coupled with resistance training (3 times per week for 15 weeks) improved physical function in a 26-year-old man with myasthenia gravis. This individual had a 7% increase in body weight, 4% increase in fat free mass, and improved peak strength up to 37%. Another investigation found that creatine supplementation improves skeletal muscle function in patients with McArdle disease.

Red meat and fish contain about two grams to five grams of creatine per pound. One study compared the effects of consuming two grams of creatine in 250-300 mL of cold water versus two grams of creatine obtained from 0.9 lbs of meat. According to the study, two grams of creatine in solution caused a quicker and greater rise in blood creatine levels, but a quicker drop also. On the other hand, eating meat caused a less dramatic rise but the increase was sustained for a longer period of time. In fact, when they compared the net increase in blood creatine, there was no difference.

Persons with Parkinson disease (PD) exhibit decreased muscular fitness including decreased muscle mass, muscle strength, and increased fatigability. Twenty patients with idiopathic PD were randomized to receive creatine monohydrate supplementation plus resistance training (CRE) or placebo (lactose monohydrate) plus resistance training (PLA), using a double-blind procedure. Creatine and placebo supplementation consisted of 20 grams per day for the first 5 days and 5 grams/day thereafter. Both groups participated in progressive resistance training (24 sessions, 2 times per week, 1 set of 8-12 repetitions, 9 exercises). They discovered that chest press strength and biceps curl strength improvement was significantly greater for the creatine supplemented group.

Short term (5 days), medium term (9 weeks) and long term (up to 5 years) oral creatine supplementation has been studied in small cohorts of athletes whose kidney function was monitored and scientists did not find any adverse effects on renal function.

Another investigation examined over a 21-month period, 98 Division IA college football players who consumed in an open label manner creatine or non-creatine containing supplements following training sessions. Subjects who ingested creatine were administered 15.75 grams/day of creatine monohydrate for five days and an average of 5 grams/day thereafter in 5-10 gram/day doses. According to this study, "long-term creatine supplementation (up to 21-months) does not appear to adversely effect markers of health status in athletes undergoing intense training in comparison to athletes who do not take creatine."

According to the position stand [?] published by the International Society of Sports Nutrition, creatine is the most effective ergogenic nutritional supplement currently available to athletes in terms of increasing high-intensity exercise capacity and lean body mass during training. Also, supplementation is not only safe, but possibly beneficial in regard to preventing injury and/or management of select medical conditions when taken within recommended guidelines. Further, there is no scientific evidence that the short or long-term use of creatine has any detrimental effects on otherwise healthy individuals. In fact, five days of creatine supplementation enhances the dynamic strength and may increase anaerobic metabolism in the lower extremity muscles, and improves performance in consecutive maximal swims in highly trained adolescent (mean age 16) fin swimmers. There are also data concerning the short and long-term therapeutic benefit of creatine supplementation in children and adults with gyrate atrophy (a result of the inborn error of metabolism with ornithine delta-aminotransferase activity), muscular dystrophy (facioscapulohumeral dystrophy, Becker dystrophy, Duchenne dystrophy and sarcoglycan deficient limb girdle muscular dystrophy), McArdle's disease, Huntington's disease and mitochondria-related diseases. Hypoxia and energy related brain pathologies (brain trauma, cerebral ischemia, prematurity) might benefit from creatine supplementation. Creatine supplementation has also been shown to lead to an improvement in various cognitive tasks.

While we exercise (more specifically intense resistance exercise) muscle mass is built by increasing mTOR (mechanistic Target of Rapamycin) and protein synthesis is enhanced as depicted in the diagram of page 8.

It is also known that certain amino acids such as leucine, isoleucine and creatine amplify the muscle building effect of resistance exercise by some of the same pathways and mechanisms and exercise.

Research shows that ordinary creatine can block 60% of myostatin in muscle, and that both leucine and creatine also activate mTOR while isoleucine plays an additive or potentially synergistic role by increasing insulin sensitivity. Isoleucine is generally overlooked in the muscle building process and given far less priority and recognition than leucine, as evidence by the BCAA formulae in the nutrition marketplace that contain and promote 2:1:1, 4:1:1, and even 8:1:1 ratios of leucine to isoleucine to valine. However, far greater value is placed on isoleucine in these inventions due to its ability to allow the body to more efficiently use insulin because of its ability to activate mTOR and because insulin is the most anabolic of all hormones including both testosterone and HGH (human growth hormone) in the human body.

It should be realized from the foregoing description that an additive and/or synergistic effect is achieved by administering to mammals adequate doses of each of the forms of creatine described herein. The serving may contain one or more of the creatine species each species or combinations thereof contributing significantly to muscle growth.

Di-Peptide Superiority.

It is well known that chain length has an effect on the absorption of biologically active peptides from the GI tract. Furthermore, we know that the potency of orally consumed peptides decreases as the chain length increases. Di-peptides and tri-peptides, but not free amino acids, are more potent than peptides with more than three amino-acids residues.

Administration of the di-peptide Leucine-IsoLeucine can increase translocation of GLU-4 to the plasma membrane. Moreover, these di- and tri-peptides have a better absorption than free amino acids. Studies also suggest that the insulin stimulates dipeptide transport and that leucine is an insulin-mimetic amino acid as well as having certain qualities of insulin like activating mTOR independent of insulin. Isoleucine is believed to enhance these processes because of an additive or synergistic effect for its ability to make insulin work better by decreasing insulin resistance and increasing insulin sensitivity.

The peptide amino acid transporter Pept-1, located in the intestinal brush border membrane, provides a potent mechanism for protein absorption in the human intestine. Studies have shown that Pept-1 transports dipeptides and tripeptides but not free amino acids or peptides with chain lengths greater than three amino acids. Conversely, these di-peptides designed to both ignite mTOR and inhibit a large percentage of myostatin for explosive muscle growth and potentially improve brain health.

Cognitive Creatine

The use of creatine to enhance muscle and performance for athletes, bodybuilders and other fitness enthusiasts is well known within these communities. However, creatine's role in brain health and the exceptional cognitive benefits it offers are not well known to the general public and/or to persons in the athletic community. No matter what sport you play having a sharper mind is critical to superior athletic performance at any level. In any sport you have to think and react superfast to achieve success. Creatine is unique in that it enhances both mind and muscle.

It is well known that molecules such as glucose and creatine provide energy for the brain. ATP (adenosine triphosphate) provides energy for cognitive function. In fact, cognitive function is completely dependent on ATP. We also know that persons with creatine transport deficiencies have impaired brain function. These persons experience dementia because creatine does not cross the BBB (blood brain barrier). We are also aware that the hippocampus exhibits the most profound neurological benefit from creatine, but is also highly susceptible to degenerative damage like that observed with aging. Science dictates that creatine is necessary for a healthy brain and to slow aging. The bigger picture here is that creatyl peptides with an added fatty acid ester side chain have the potential to readily cross the BBB. For these reasons these new super creatine peptides could be the next big breakthrough in regard to pharmaceutical smart drugs and also have the potential to retard and even reverse aging.

Research shows that both vegetarians (this population does not consume animal proteins that contain significant amounts of creatine) and elderly persons given creatine showed significant improvement in intelligence, IQ scores and improved ability to repeat longer sequences of numbers from memory.

The brain needs creatine. Creatine deficiency in the brain results in mental retardation. There is something known as creatine transporter deficiency which is caused by an impairment of the SLC6A8 creatine transporter. When SLC6A8 stops working creatine can no longer penetrate the brain. However, adding a long chain fatty ester to a creatine allows creatine to penetrate into neuronal cells in the brain even when no SLC6A8 is available. One study even showed that a specific dodecyl creatine ester resulted in a 20 fold increase in human fibroblasts compared with the endogenous creatine content.

Thus, creatine is known to provide many benefits, including enhancing athletic performance in the strength-power sports, promoting gains in lean body mass and muscle fiber hypertrophy (growth), helping neuromuscular function in those with various metabolic diseases, improving memory, assisting various neural functions. Further, creatine has long-term safety data.

Creatine is typically offered in tablet, capsule and powder form; however, powder is currently form is most common form of creatine sold in retain stores. More recently, U.S. Pat. No. 8,445,466 was granted giving birth to the first aqueous stable carbonated creatyl (creatine) beverage which is now also for sale in the world's largest health food store retailers. However, most forms of creatine and all its derivatives suffer from either very low solubility and/or other problems. For example creatine HCl, can cause potential problems to the teeth, mouth and esophagus because of its high acid content. Another example of a creatine that suffers from very poor solubility (which, ironically, is by far the most popular of all creatine varieties) is creatine monohydrate. Solubility is a rate-limiting factor of bioavailability. Since drugs and/or nutrients must be soluble to achieve Gastro Intestinal Tract (GIT) absorption, the majority of drug modification and formulation strategies focus on improving solubility. The higher the concentration of drug in solution, and the longer the drug stays in solution as it travels through the GIT, the higher the absorption and bioavailability.

A drug's solubility/rate-of-dissolution is often related to its in vivo performance (bioavailability). Therefore, prediction and measurement of these properties becomes critical in characterizing new drug candidates and the formulations in which they are developed. The establishment and understanding of IVIVC's (in-vitro-in-vivo correlations) of drug candidates formulated into dosage forms begins with measurement of the drug's solubility and dissolution rate.

BRIEF SUMMARY OF THE INVENTION

Accordingly, the primary object of the present invention is provide a creatine derivative with enhanced solubility that will result in greater bioavailability and greater in vivo performance. Acetylated creatine in accordance with the principles of the invention may be optionally be bonded to an amino acid or di-peptide and may be optionally comprise aliphatic esters and/or polymers depending on the intended application.

In one embodiment, the principles of other present invention relate to N-acetyl creatine, wherein an acetyl group replaces an active hydrogen of the amino group in creatine, and also to creatyl peptides wherein an amino acid is bonded to acetylated creatine. The principles of the invention further relate to N-acyl creatines, wherein an acyl group replaces an active hydrogen in the amino group in creatine and to creatyl peptides.

In another embodiment, the principles of the invention relate to N,N-diacyl creatines, wherein two acyl group are attached to two amino groups in creatine and creatyl peptides.

In another embodiment, the principles of the invention relate to N-acetyl creatine, N-acyl creatines, N,N-diacyl creatine, N-acetyl creatine aliphatic esters and to N-acetyl creatine amino acid dipeptides and their aliphatic esters, which may have enhanced bioavailability to mammals when in solution.

In one embodiment, creatine derivatives may be formed by acetylating creatine. The creatine derivative compound may be more soluble and more bioavailable than other creatine compounds.

In another embodiment, a creatyl peptide may have increased solubility and bioavailability. N-acetyl-Leucine has extremely poor solubility in an aqueous medium. In the case of acetylated leucine, the solubility of free leucine is ten times greater than the solubility of N-acetyl-Leucine. In contrast, the acetylation of creatine results in a massive and significant increase in solubility. In the case of N-acetyl creatine, the subject of this invention, the acetylated creatine entity has become 30 times more soluble than the parent compound creatine.

In another embodiment, acetyl-creatine is bonded to an aliphatic ester or an amino acid, creating a creatine derivative that is more bioavailable than other creatine compounds in the art.

In another embodiment, one or more of the creatine derivatives may by provided as a powder, tablet, capsule, buccal, injectable, topical as a gel, lotion or cream, transdermal patch, and other non-aqueous forms suitable for use by mammals.

In one embodiment, a composition in accordance with the principles of the invention may comprise N-Acetyl Creatine, N-acyl creatines, N,N-diacyl creatines, and/or N-acetyl creatine species in the form of acetyl creatyl peptides or their aliphatic esters, and non-aqueous vehicles or carriers. A composition may also include excipients, and other biologically active compounds.

It is therefore an object of the present invention to provide creatine derivatives suitable for delivering creatine and/or one or more peptides to a mammalian system in a form which improves the bioavailability of the components of the composition.

These and other objects and advantages of the present invention will become apparent from a reading of the attached specification and appended claims. There has thus been outlined, rather broadly, the more important features of the invention in order that the detailed description thereof that follows may be better understood, and in order that the present contribution to the art may be better appreciated. There are features of the invention that will be described hereinafter and which will form the subject matter of the claims appended hereto.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
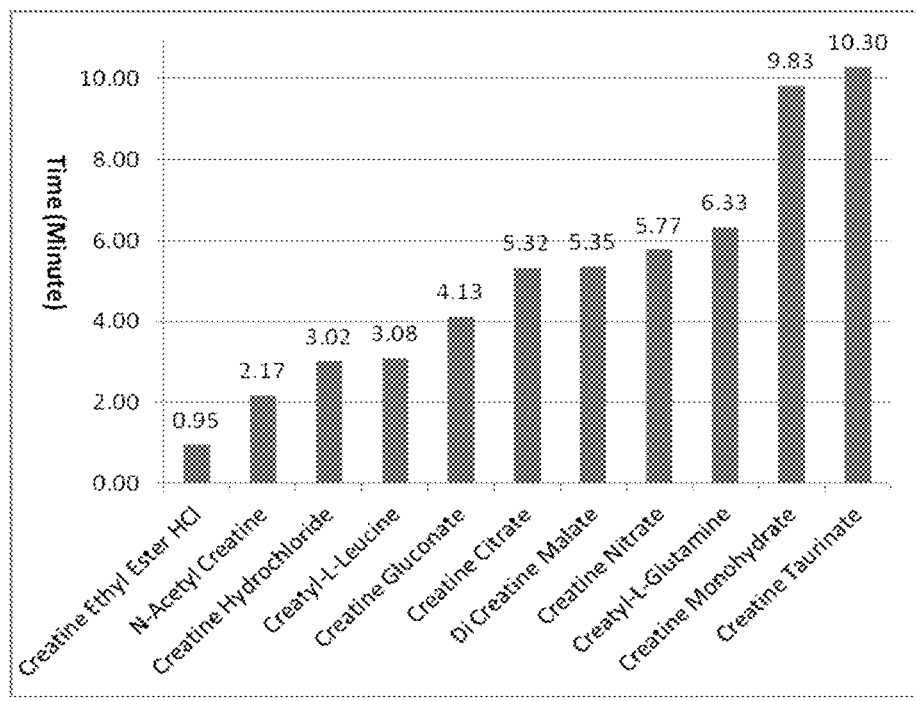
FIG. 1 is a graph showing solubility data for creatine derivatives.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

This invention relates more specifically to N-acetyl creatine, wherein an acetyl group replaces an active hydrogen of the amino group in creatine and to creatyl peptides wherein an amino acid is chemically attached to the acetylated creatine molecule. It further relates to N-acyl creatines, wherein an acyl attachment replaces an active hydrogen in the amino group in creatine and to creatyl peptides, herein acyl group refers to carboxylic acid, including saturated, monounsaturated, polyunsaturated fatty acid, for example: propionoic acid, docosahexaenoic acid (DHA), or eicosapentaenoic acid (EPA). In addition, it relates to N,N-diacyl creatines, wherein two acyl group are attached to two amino groups in creatine and creatyl peptides.

This invention further relates to N-acetyl creatine, N-acyl creatines, N,N-diacyl creatine, N-acetyl creatine aliphatic esters and to N-acetyl creatine amino acid dipeptides and their aliphatic esters, which are more bioavailable to mammals than other creatine derivative.

As used herein, a "N-acetyl-creatine species" may refer to any of N-acetyl creatine, N-acyl creatines, N,N-diacyl creatine, N-acetyl creatine aliphatic esters and to N-acetyl creatine amino acid dipeptides and their aliphatic esters, including Creatyl-L-Leucine, Creatyl-L-Isoeucine, Creatyl-Leucine-L-Leucine, Creatyl-L-Leucine-L-Isoleucine singly or in combination.

As used herein, "nucleotide species" may refer to nucleotides, oligonucleotides, as well as the monophosphate, diphosphate, triphosphate and cyclic derivatives of nucleotides.

As used herein, "peptides" may refer to amino acids, peptides, di-, tri- and oligo peptides and protein derivatives.

As used herein, "protein isolates" may refer to egg, collagen, plant and/or milk-based proteins, either singly or in combination, acid stable protein isolates, or a combination or blend of protein isolates, concentrates and hydrolyzates and caseins in micellar forms.

Figure 2:
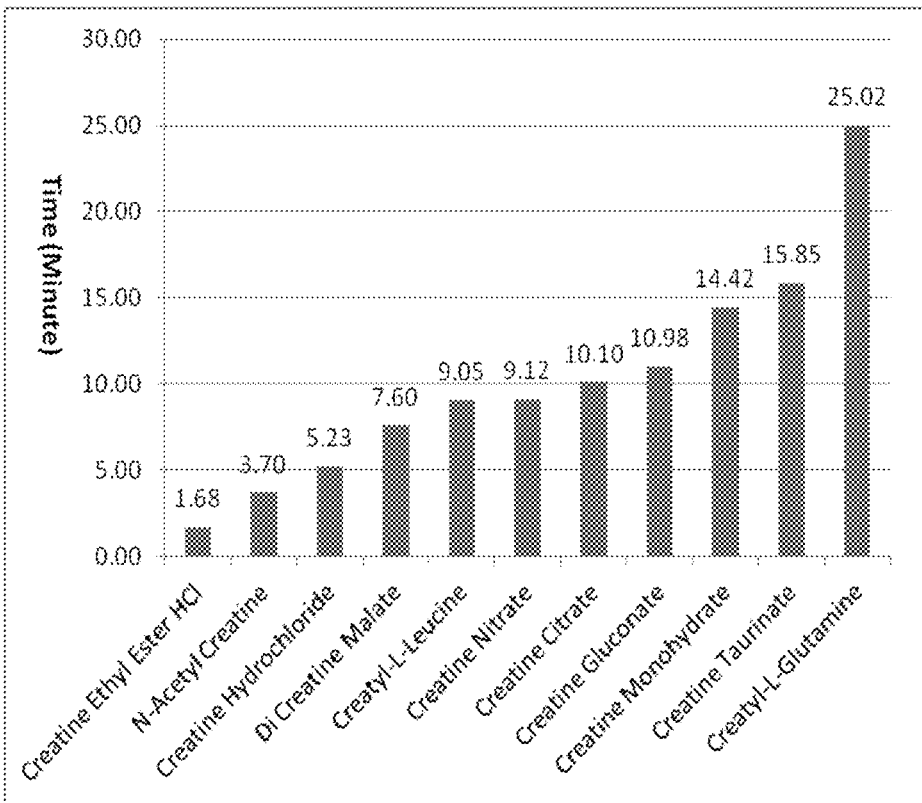
FIG. 2 is a graph showing solubility data for creatine derivatives.

In accordance with the principles of the invention, a creatine species formed by acetylating creatine may be more soluble than other creatine compounds and more bioavailable than other creatine compounds known in the art, as shown in FIGS. 1 and 2.

As may be seen in FIGS. 1 and 2, N-acetyl-Leucine exhibits extremely poor solubility in an aqueous medium. In this case of acetylated leucine, the solubility of free leucine is ten times greater than the solubility of N-acetyl-Leucine. In contrast, acetylation of creatine results in a massive and significant increase in solubility. N-acetyl creatine may be 30 times more soluble than creatine.

Acetylated creatine in accordance with the invention, may have increased bioavailable and solubility.

Creatine derivatives, including N-acetyl-creatine species, may be provided as nutritional supplements in the forms of powder, tablet, capsule, buccal, injectable, topical as a gel, lotion or cream, transdermal patch, and other non-aqueous forms suitable for use by mammals.

Disclosed is N-acetyl creatine, and creatyl peptides suitable for oral administration to mammalian subjects, including humans. N-acetyl creatine has the structure:

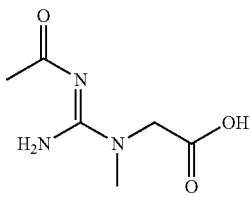

(I)

The synthesis of N-Acetyl Creatine is achieved as follows: Sarcosine was treated with acetyl protected guanidinylation reagents to afford N-acetyl creatine.

Other N-acetyl creatine species which comprised this invention include:

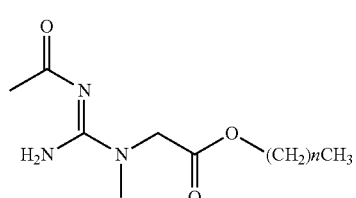

(II)

N-Acetyl creatine aliphatic ester
$n$ = from 0 to 21

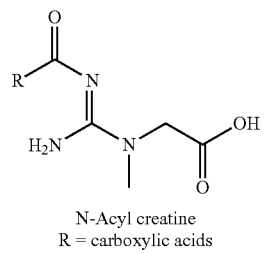

(III)

N-Acyl creatine
R = carboxylic acids

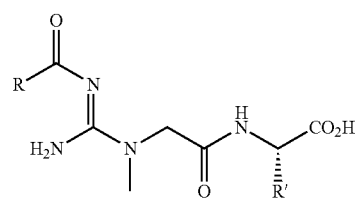

(IV)

N-Acyl creatyl amino acid dipeptides
R = carboxylic acids
R' = amino acids

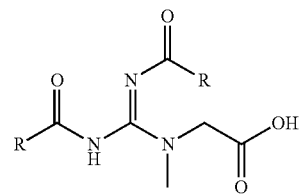

(V)

N,N-Diacyl creatine
R = carboxylic acids

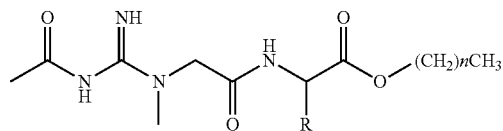

(VI)

N-Acetyl creatyl dipeptides aliphatic ester
$n$ = from 0 to 21
R = amino acids

The materials described by formulae (I), (II), (III), (IV), (V), and (VI) above, and the corresponding text in the descriptions, including any and all of its forms, are N-acetyl creatine species, and are, as such, the subject of the present invention.

To prepare a composition according to the principles of this invention, one may add a desired amount of N-acetyl creatine species to a selected group of non-aqueous excipients and sufficient mixing may cause a uniform blend of the N-acetyl creatine to afford a non-aqueous composition. In one embodiment, the total concentration of N-acetyl creatine species in a non-aqueous solution provided hereby may be any amount between about 0.1 gram and about 22 grams (or more), including all amounts therebetween.

According to another embodiment, the total concentration of N-acetyl creatine species in a non-aqueous blend provided hereby may be any amount between about 1 gram and about 10 grams, including all amounts there between.

According to another embodiment, the total concentration of N-acetyl creatine species in a non-aqueous composition provided hereby may be any amount between about 1 gram and about 5 grams including amounts therebetween.

According to another embodiment, the total concentration of N-acetyl creatine species in a non-aqueous composition provided hereby may be any amount between about 0.01 g and about 1 gram including all amounts therebetween. In an alternate embodiment, the N-acetyl creatine species may be added to a natural powder beverage in any amount provided that upon reconstitution an aqueous solution or suspension results.

| Solubility Data for Various Types of Creatine in HCl | |
|---|---|
| Dissolution Media (pH = 1.2) | 0.1N HCl in Water |
| Media Amount | 900 ml |
| Dissolution Temperature | 73 C. |
| RPM | 75 |
| Sample Weight | 1.000 Gram |
| Sample Description | Time (Minutes) |
| Creatine ethyl ester HCl | 0.95 |
| N-acetyl creatine | 2.17 |
| Creatine HCl | 3.02 |
| Creatyl-L-Leucine | 3.08 |
| Creatine Gluconate | 4.13 |
| Creatine Citrate | 5.32 |
| Di-Creatine Malate | 5.35 |
| Creatine Nitrate | 5.77 |
| Creatyl-L-Glutamine | 6.33 |
| Creatine Monohydrate | 9.83 |
| Creatine Taurinate | 10.30 |

| Solubility Data for Various Types of Creatine in Water | |
|---|---|
| Dissolution Media (pH = 1.2) | Distilled Water |
| Media Amount | 900 ml |
| Dissolution Temperature | Room Temperature |
| RPM | 75 |
| Sample Weight | 1.000 Gram |
| Sample Description | Time (Minutes) |
| Creatine ethyl ester HCl | 1.68 |
| N-acetyl creatine | 3.70 |
| Creatine HCl | 5.23 |
| Di Creatine Malate | 7.60 |
| Creatine-L-Leucine | 9.05 |
| Creatine Nitrate | 9.12 |
| Creatine Citrate | 10.10 |
| Creatine Gluconate | 10.98 |
| Creatyl Monohydrate | 14.42 |
| Creatine Taurinate | 15.85 |
| Creatine-L-Glutamine | 25.02 |

These tables show the solubility of creatine and creatine derivatives compared to N-acetyl creatine in 0.1N Hydrochloride (HCl) at 37° C. As may be seen, 1 gram of N-acetyl creatine dissolves faster than other creatine derivatives, except creatine ethyl ester HCl, designated Creatine EE Hcl—(High Creatine Conversion) in FIG. 1. However, this shorter dissolution time may be deceiving. Creatine ethyl ester HCL does not actually dissolve faster in aqueous media. Instead, Creatine ethyl ester HCl decomposes into creatinine in a matter of 2 to 3 minutes. Creatinine is an excretory byproduct produced from the breakdown of creatine phosphate and offers none of the numerous benefits of creatine. In other words, Creatine ethyl ester HCl is unstable and its rapid conversion to creatinine makes it ineffective in delivering bioavailable creatine to the body.

The dissolution of 1 gram of N-acetyl creatine is faster than the other creatine derivatives shown, and the creatine remains stable in solution, not decomposing as creatine ethyl ester HCl does.

The dissolution of 1 gram of N-acetyl creatine in a substantially pH neutral aqueous solution is faster than the other creatine derivatives except for creatine ethyl ester HCL which has the disadvantage of not being chemically stable as discussed above.

Solubility Data for L-leucine Versus N-acetyl L-leucine

| Dissolution Media | Distilled Water |
|---|---|
| Media Amount | 900 ml |
| Dissolution Temperature | Room Temperature |
| RPM | 75 |
| Sample Weight | 1.000 g |
| Sample Description | Time (Minutes) |
| Leucine | 12.82 |
| N-Acetyl Leucine | 120.17 |

The solubility of N-acetyl creatine in water is 400 grams/1 liter. This represents a 30-fold increase with respect to creatine monohydrate with a solubility of about 13 grams in 1 liter.

As may be seen from the tables and FIGS. 1 and 2, leucine is also a compound with very low water solubility. Furthermore, not only does creatine portion of the creatyl molecule become significantly more soluble than standard creatine (creatine monohydrate), L-leucine also becomes significantly more soluble in the creatyl form as it is seen in the Creatyl-L-Leucine molecule. Thus in one single compound two benefits may be achieved i.e., enhanced solubility of both creatine and of leucine. Creatine and leucine may generally have a greater impact than other amino acids in regard to increasing muscle hypertrophy, muscle strength, muscle repair, muscle energetics, mTOR (more specifically, mTORC1) activation, MPS (muscle protein synthesis), anabolism, and also in myostatin inhibition and reduction, anti-catabolism, preventing MPB (muscle protein breakdown) etc. The Creatyl-L-Leucine species may also possess the uptake benefits of di-peptides.

Similarly, glutamine also has low solubility and rapidly converts to undesirable glutamic acid when combined with water. Likewise creatine converts to creatinine over time when combined with water. Both glutamine and creatine can be delivered in a stable and soluble form as the creatyl di-peptide: creatyl-L-glutamine. Consequently, creatyl-L-glutamine may provide the benefits of enhanced aqueous stability of both creatine and of glutamine. This may allow creatyl-L-glutamine to be provided in products such as ready-to-drink water-based beverages such as sports drinks and beverages for preventing muscle wasting and improve or stabilize brain health in persons confined to a hospital and in a multitude of different medical applications such use as in IV drips, injectable delivery systems etc.

In addition, a composition according to this invention may also include nutritional adjuvant materials including flavoring agents, colorants, viscosity modifiers, preservatives, chelating agents, antioxidants, surface modifiers and other nutritional adjuvant materials. Other nutritional adjuvant materials include any substance which is generally recognized as promoting the health or function of a mammalian organism, including humans, or benefiting a composition useful thereof in terms of its efficacy, appearance, stability, consistency, aroma, or viscosity. Such substances include other amino acids and their salts, vitamins, minerals, essential fatty acids, enzymes, mono-glycerides, di-glycerides, tri-glyceride ester oils (including, for example vegetable oils and animal fats) emulsifiers, hydrolyzed proteins, whey protein, stabilizers, flow modifiers, viscosity improvers, chelating agents, enzymes, and surfactants, whether anionic, cationic or nonionic. The total amount of the one or more nutritional adjuvant materials above present in a composition according to this invention is present in any amount between about 0.01% and about 75% by weight based on the total weight of said composition, including all percentages and ranges of percentages therebetween.

In addition to ingredients classified as adjuvant materials, a composition according to this invention may also comprise one or more natural powder beverages. A natural powder beverage for reconstitution, as used herein, is a beverage suitable for human or animal consumption which contains the pulp, extract or any other constituent of a naturally-occurring fruit, vegetable, or animal product whether from the wild, cultured, cultivated on a farm or otherwise domesticated by Man. Natural powder beverages include without limitation materials such as dried milk products, dried soy products, dried citrus fruit juices, dried non-citrus fruit juices, and dried vegetable juices, or components of any of the foregoing, wherein said natural beverages are present in any effective amount to impart flavor to the compositions, which may be any amount between about 0.1% and about 99% by weight based on the total weight of said composition, including all percentages and ranges of percentages there between.

In addition to ingredients containing adjuvant materials, a composition according to the principles of the invention may alternately comprise one or more synthetic beverages. A synthetic beverage is any beverage which is not a natural beverage.

In general, a composition according to the principles of the invention may be provided by combining and mixing the ingredients selected, including any N-acetyl creatine species and any desired quantity of any one or more other ingredients specified herein.

A composition according to the principles of the invention may be made quite palatable by a mammalian subject, including human subjects desiring to administer the N-acetyl creatine species compound orally in a non-aqueous mixture. Typical serving sizes may be any serving size in the range of about 1 milligram to about 50 grams, in an aqueous solution that is from about 20 mL to about 2,500 mL in volume. The composition of N-acetyl creatine in a non-aqueous media or vehicle according to this invention can be made for re-constitution in which N-acetyl creatine may exceed 50 grams per liter and concentrations at or near the solubility limit are herein provided by contacting excess amounts of the N-acetyl creatine in contact with water or an aqueous solution to provide a solution saturated with N-acetyl creatine. Such saturated solutions may then be diluted slightly, to afford a concentrate from which other N-acetyl creatine containing compositions may be conveniently provided.

The following are examples that illustrate procedures for practicing the invention. These examples should not be construed as limiting.

EXAMPLE 1

Powder Compositions

A powder composition (for reconstitution) comprising N-acetyl creatine or any N-acetyl creatine species, said composition comprising a suitable non-aqueous solvent or vehicle, a preservative, a physical stabilizing ingredient, one or more surfactants. The composition may also contain nucleotides, oligonucleotides, the monophosphates, diphosphates, triphosphates and cyclic derivatives of these nucleotides, and amino acids, vitamins and vitamin-like isoprenoids, peptides and one or more additional components selected from the group consisting of: lipids, starches, carbohydrates, polyols, minerals, electrolytes, amino trace elements, colorings, flavors, artificial sweeteners, and anti-oxidants

EXAMPLE 2

Liquid Ready-to-Drink Compositions

An oral liquid composition for buccal sublingual administration comprising N-acetyl creatine or any N-acetyl creatine species, said composition comprising a suitable non-aqueous solvent or vehicle, a preservative, a physical stabilizing ingredient, one or more surfactants. The composition may also contain nucleotides, oligonucleotides, the monophosphates, diphosphates, triphosphates and cyclic derivatives of these nucleotides, and amino acids, vitamins and vitamin-like isoprenoids, peptides and one or more additional components selected from the group consisting of: lipids, starches, carbohydrates, polyols, minerals, electrolytes, amino trace elements, colorings, flavors, artificial sweeteners, and anti-oxidants.

EXAMPLE 3

Oral Composition—Solid

An oral solid composition in the form of a capsule (liquid capsule) with a liquid composition as fill material for oral administration of N-acetyl creatine or any N-acetyl creatine species containing from about 1% to about 5% of Water, said liquid fill material composition comprising a suitable lipophilic solvent or vehicle, a hydrophilic non-aqueous vehicle, from about 1% to about 5% of water, a preservative, a physical stabilizing ingredient, one or more surfactants. The composition may also contain nucleotides, oligonucleotides, the monophosphates, diphosphates, triphosphates and cyclic derivatives of these nucleotides, and amino acids, vitamins and vitamin-like isoprenoids, peptides and one or more additional components selected from the group consisting of: lipids, medium and short chain triglycerides, starches, polyols, carbohydrates, minerals, electrolytes, amino trace elements, colorings, and anti-oxidants.

EXAMPLE 4

Powder Composition—Oral Administration

A powder composition for oral administration of N-acetyl creatine or any N-acetyl creatine species containing from 1 gram to 100 grams of protein and from 1 gram to 100 grams of carbohydrates per serving comprising N-acetyl creatine or any N-acetyl creatine species. The composition comprising egg, collagen, plant and/or milk-based proteins either singly or in combination in a suitable aqueous solvent or vehicle, a non-aqueous vehicle, a preservative, a physical stabilizing ingredient, one or more surfactants. The composition comprising an acid stable protein isolates, or a combination or blend of protein isolates, concentrates and hydrolyzates and caseins in micellar forms, a suitable aqueous solvent or vehicle, a non-aqueous vehicle, a preservative, a physical stabilizing ingredient, one or more surfactants. The composition may also contain nucleotides, oligonucleotides, the monophosphates, diphosphates, triphosphates and cyclic derivatives of these nucleotides, and amino acids, vitamins and vitamin-like isoprenoids, peptides and one or more additional components selected from the group consisting of: lipids, starches, carbohydrates, polyols, minerals, electrolytes, amino trace elements, colorings, flavors, artificial sweeteners, and anti-oxidants.

EXAMPLE 5

Injectable Compositions

A lyophilized injectable composition for human consumption said composition being isotonic and sterile in nature comprising N-acetyl creatine or any N-acetyl creatine species, said injectable preparation with a pH of about 3, being substantially stable at room temperature for short term storage conditions, stable at 104° Fahrenheit (40 Celsius degrees) and stable for longer term at 39° Fahrenheit (4 Celsius degrees) in coolers so that it can be stored under refrigeration conditions. The composition comprising a suitable aqueous solvent, a preservative, and/or a physical stabilizing ingredient. The composition may also contain nucleotides, oligonucleotides, the monophosphates, diphosphates, triphosphates and cyclic derivatives of these nucleotides, and amino acids, peptides, proteins and carbohydrates.

EXAMPLE 6

Topical Gel Compositions

An anhydrous gel topical composition for skin application in humans and animals said composition being clear or slightly opaque and having a gel consistency so that it can be spread on skin surface comprising N-acetyl creatine or any N-acetyl creatine species, said gel being substantially stable at room temperature for normal warehouse storage conditions, stable at 104° Fahrenheit (40 Celsius degrees) for shipping in hot weather trucks and/or overseas containers, and stable at 39° Fahrenheit (4 Celsius degrees) in coolers so that it can be stored under refrigeration conditions. The composition comprising a suitable non-aqueous solvent, a preservative, a polymer for imparting consistency and/or a physical stabilizing ingredient. The composition may also contain nucleotides, oligonucleotides, the monophosphates, diphosphates, triphosphates and cyclic derivatives of these nucleotides, and amino acids, vitamins and vitamin-like isoprenoids, peptides, proteins and carbohydrates.

EXAMPLE 7

Deep-Penetrating Transdermal Compositions

A deep-penetrating transdermal composition for application in humans and animals said composition being a non-aqueous solution, a gel-like system or an opacified gel-like system and having a consistency so that it can be spread on skin surface comprising N-acetyl creatine or any N-acetyl creatine species, said transdermal composition being substantially stable at room temperature for normal warehouse storage conditions, stable at 104° Fahrenheit (40 Celsius degrees) for shipping in hot weather trucks and/or overseas containers, and stable at 39° Fahrenheit (4 Celsius degrees) in coolers so that it can be stored under refrigeration conditions. The composition comprising a suitable non-aqueous solvent, one or more penetrating enhancers, a preservative, a physical stabilizing ingredient, one or more surfactants, moisturizers. The composition may also contain nucleotides, oligonucleotides, the monophosphates, diphosphates, triphosphates and cyclic derivatives of these nucleotides, and amino acids, vitamins and vitamin-like isoprenoids, peptides, proteins and carbohydrates.

EXAMPLE 8

Transdermal Patch Delivery System Compositions

A transdermal patch delivery system comprising of a liner, an adhesive, a backing and a non-aqueous liquid reservoir composition. The non-aqueous liquid reservoir composition being a solution or a suspension comprising N-acetyl creatine or any N-acetyl creatine species, said transdermal patch being substantially stable at room temperature for normal warehouse storage conditions, stable at 104° Fahrenheit (40 Celsius degrees) for shipping in hot weather trucks and/or overseas containers, and stable at 39° Fahrenheit (4 Celsius degrees) in coolers so that it can be stored under refrigeration conditions. The composition comprising a suitable non-aqueous solvent, one or more penetrating enhancers, a preservative, a physical stabilizing ingredient, one or more surfactants. The composition may also contain nucleotides, oligonucleotides, the monophosphates, diphosphates, triphosphates and cyclic derivatives of these nucleotides, and amino acids, vitamins and vitamin-like isoprenoids, peptides, proteins and carbohydrates.

A composition as provided herein may be administered chronically. As used herein, "chronically" has its normal meaning, which generally means repeated ingestion over a period of several days, several weeks or even several months. "Chronic" is generally not acute.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. This includes subject matter defined by any combination of any one of the various claims appended hereto with any one or more of the remaining claims, including the incorporation of the features and/or limitations of any dependent claim, singly or in combination with features and/or limitations of any one or more of the other dependent claims, with features and/or limitations of any one or more of the independent claims, with the remaining dependent claims in their original text being read and applied to any independent claims so modified. This also includes combination of the features and/or limitations of one or more of the independent claims with features and/or limitations of another independent claim to arrive at a modified independent claim, with the remaining dependent claims in their original text being read and applied to any independent claim so modified. Accordingly, the present invention is intended to cover all such modifications and alterations and is not intended to be necessarily limited by any one or more particular strict interpretations of the claims which now follow.

Whereas, the present invention has been described in relation to the drawings attached hereto, it should be understood that other and further modifications, apart from those shown or suggested herein, may be made within the spirit and scope of this invention. Descriptions of the embodiments shown in the drawings should not be construed as limiting or defining the ordinary and plain meanings of the terms of the claims unless such is explicitly indicated.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The invention claimed is:

1. A composition for delivering bio-available creatine comprising:
    an N-acetyl creatine species;
    a non-aqueous solvent;
    a preservative;
    a physical stabilizing ingredient;
    one or more surfactants;
    wherein the N-acetyl creatine species comprises a N-Acyl creatyl amino acid dipeptide.

2. The composition of claim 1 further comprising one or more adjuvants selected from the group consisting of nucleotide species, peptides, protein isolates, lipids, starches, carbohydrates, polyols, minerals, electrolytes, amino trace elements, colorings, flavors, artificial sweeteners, anti-oxidants, vitamins and vitamin-like isoprenoids.

3. The composition of claim 2 wherein the composition further comprises water and the composition is an aqueous solution.

4. The composition of claim 1 wherein the composition further comprises a liquid fill material comprising:
    a lipophilic solvent;
    a hydrophilic non-aqueous vehicle;
    1% to about 5% of water;
    a preservative;
    a physical stabilizing ingredient; and,
    one or more surfactants;
    wherein the composition is provided in the form of a capsule.

5. The composition of claim 1 further comprising one or more protein isolates.

6. The composition of claim 5 further comprising one or more adjuvants selected from the group consisting of nucleotide species, peptides, lipids, starches, carbohydrates, polyols, minerals, electrolytes, amino trace elements, colorings, flavors, artificial sweeteners, anti-oxidants, vitamins and vitamin-like isoprenoids.

7. A composition for delivering bio-available creatine comprising:
    an N-acetyl creatine species;
    a suitable non-aqueous solvent;
    a preservative;
    a polymer for imparting consistency; and,
    a physical stabilizing ingredient;
    wherein the composition is substantially stable at room temperature, stable at 104° Fahrenheit, and stable at 39° Fahrenheit; and,
    wherein the N-acetyl creatine species comprises N,N-Diacyl creatine.

8. The composition of claim 7 further comprising one or more adjuvants selected from the group consisting of nucleotide species, peptides, lipids, starches, carbohydrates, polyols, minerals, electrolytes, amino trace elements, colorings, flavors, artificial sweeteners, anti-oxidants, vitamins and vitamin-like isoprenoids.

9. The composition of claim 8 further comprising one or more penetrating enhancers and a moisturizer; wherein the composition has a gel consistency and may be topically applied to the skin as a gel.

10. The composition of claim 9 further comprising one or more penetrating enhancers and a moisturizer; wherein the composition is contained in the reservoir of a transdermal patch delivery system comprising the reservoir, a line, an adhesive and a backing.

11. The composition of claim 2 further comprising one or more natural products selected from the group consisting of dried milk products, dried soy products, dried citrus fruit juices, dried non-citrus fruit juices, and dried vegetable juices.

12. A composition for delivering bio-available creatine comprising:
    an N-acetyl creatine species;
    a non-aqueous solvent;
    a preservative;
    a physical stabilizing ingredient;
    one or more surfactants;
    wherein the N-Acetyl creatine species comprises a N-Acyl creatyl dipeptide aliphatic ester.

* * * * *